United States Patent [19]

Truppe

[11] Patent Number: 5,823,958
[45] Date of Patent: Oct. 20, 1998

[54] SYSTEM AND METHOD FOR DISPLAYING A STRUCTURAL DATA IMAGE IN REAL-TIME CORRELATION WITH MOVEABLE BODY

[76] Inventor: Michael Truppe, 5 Triad Center, Suite 580, Salt Lake City, Utah 84180

[21] Appl. No.: 259,986

[22] Filed: Jun. 15, 1994

Related U.S. Application Data

[63] Continuation-in-part of Ser. No. 213,188, Mar. 15, 1994, Pat. No. 5,678,546, which is a continuation of Ser. No. 792,892, Nov. 15, 1991, abandoned.

[30] Foreign Application Priority Data

| | | | |
|---|---|---|---|
| Nov. 26, 1990 | [AT] | Austria | A2397/90 |
| Nov. 26, 1990 | [AT] | Austria | A2398/90 |

[51] Int. Cl.$^6$ ........................................ A61G 5/05
[52] U.S. Cl. .................. 600/426; 600/595; 128/898
[58] Field of Search .............................. 128/653.1, 660.1, 128/782, 774; 378/4, 20, 21, 28, 29, 37, 62, 63, 98, 204, 210; 364/413.01, 413.02, 413.13, 413.14, 413.19, 413.21, 413.22, 413.25, 460; 356/1; 340/980

[56] References Cited

U.S. PATENT DOCUMENTS

| | | | |
|---|---|---|---|
| 3,737,217 | 6/1973 | Haines et al. | 128/745 |
| 4,197,855 | 4/1980 | Lewin | 128/653 |
| 4,550,984 | 11/1985 | Reymond . | |
| 4,722,056 | 1/1988 | Roberts et al. . | |
| 4,817,433 | 4/1989 | Sato . | |
| 4,832,049 | 5/1989 | Matsushita et al. | 128/781 |
| 4,922,909 | 5/1990 | Little et al. | 128/630 |
| 4,930,888 | 6/1990 | Freisleben et al. . | |
| 4,987,412 | 1/1991 | Vaitekunas et al. . | |
| 4,988,976 | 1/1991 | Lu | 340/461 |

(List continued on next page.)

FOREIGN PATENT DOCUMENTS

| | | |
|---|---|---|
| 384544B | 11/1987 | Austria . |
| 0077193B1 | 4/1983 | European Pat. Off. . |
| 0119660A1 | 9/1984 | European Pat. Off. . |
| 0488987A1 | 6/1992 | European Pat. Off. . |
| 2545349A1 | 11/1984 | France . |
| 3406179C1 | 9/1985 | Germany . |
| 3532730A1 | 3/1987 | Germany . |
| 3807578A1 | 9/1989 | Germany . |
| 4134481A1 | 4/1993 | Germany . |

OTHER PUBLICATIONS

Maekawa et al., "Measurement of the Upper Limb Motion by a Magnetic Sensor and Its Application to Kinesiology Studies," pp. 1445–1446, IEEE Engineering in Medicine and Biology Society 11th Annual International Conference, 1989.

J. Gybels, D. Vandermeulen, P. Suetens, G. Marchal and G. Wilms, "A Prototype Medical Workstation for Computer–Assisted Stereotactic Neurosurgery." pp. 493–496, 10th meeting of the World Society for Stereotactic and Functional Neurosurgery, Maebashi, Japan, Oct. 1989.

(List continued on next page.)

*Primary Examiner*—Guy V. Tucker
*Attorney, Agent, or Firm*—Dale E. Hulse; Berne S. Broadbent

[57] ABSTRACT

A system and method including a transparent display positioned between an object and an observer on which displays a superimposed data image transformed from structural data by calculating the parameters of a three dimensional matrix with information collected from position sensors. The mathematical parameters of the three dimensional matrix are defined in order to transform the structural image data into the perspective display data. Once the parameters of the three dimensional matrix are established, any points of the structural image can be shown on the display as a virtual image corresponding to the points on the object in real time.

3 Claims, 2 Drawing Sheets

U.S. PATENT DOCUMENTS

| | | |
|---|---|---|
| 5,007,428 | 4/1991 | Watmough . |
| 5,072,218 | 12/1991 | Spero et al. . |
| 5,089,816 | 2/1992 | Holmes, Jr. ............................ 340/995 |
| 5,099,846 | 3/1992 | Hardy . |
| 5,099,859 | 3/1992 | Bell ....................................... 128/781 |
| 5,186,174 | 2/1993 | Schlondorff et al. . |
| 5,279,309 | 1/1994 | Taylor et al. ........................... 128/782 |
| 5,375,610 | 12/1994 | LaCourse et al. ..................... 128/782 |

OTHER PUBLICATIONS

P. Haigron and R. Collorec, "3D Surface Reconstruction Using Strongly Distorted Stereo Images," pp. 1050–1051, Annual International Conference of the IEEE Engineering in Medicine and Biology Society, vol. 13, No. 3, 1991.

Amami Kato, Toshiki Yoshimine and Hayakawa, "A Frameless, Armless Navigational System for Computer Assisted Neurosurgery." pp. 845–849, *J. Neurosurg.*, vol. 74, May, 1991.

Michael Bajura, Henry Fuchs and Ryutarou Ohbuchi, "Merging Virtual Objects with the Real World: Seeing Ultrasound Imagery within the Patient." pp. 203–209, *Computer Graphics*, vol. 26.2, Jul., 1992.

Pavel Houdek, James Schwade, Christopher Serago, Howard Landy, Vincent Pisciotta, Xiaodong Wu, Arnold Markoe, Alan Lewin, Andre Abitbol, Joanne Bujnoski, Evelyn Marienberg, Jeffrey Fiedler and Murray Ginsberg, "Computer Controlled Stereotaxic Radiotherapy Systems." pp. 175–180, *Int. J. Radiation Oncology Biol. Phys.*, vol. 22, No. 1, 1992.

SYSTEM AND METHOD FOR DISPLAYING A STRUCTURAL DATA IMAGE IN REAL-TIME CORRELATION WITH MOVEABLE BODY

BACKGROUND

1. Related Applications

This application is a continuation-in-part of my application Ser. No. 08/213,188, filed on Mar. 15, 1994 for METHOD FOR DISPLAYING MOVEABLE BODIES, now U.S. Pat. No. 5,678,546 which is a continuation of prior application Ser. No. 07/792,892, filed on Nov. 15, 1991 for METHOD FOR DISPLAYING MOVEABLE BODIES, now abandoned.

2. The Field of the Invention

This invention relates to systems and methods for displaying a structural data image in correlation with a moveable object. More particularly, the invention relates to a method for displaying data structures that are associated to an object in space by continuously tracking the position of an observer's head relative to the object, and by computation of a perspective display of the data depending on the position of the observer and visualization on a transparent display device.

3. The Background Art

It is often required in the field of engineering and medicine to correlate a physical object with different image data representations of the object. For example, the image data representations help a physician or an engineer to view the object with information which cannot be obtained by human eyes.

A popular data representation commonly used by physicians is an x-ray image. Using an x-ray image of a region of interest, a physician can see the bone structures of a patient which are not readily perceived with the eyes alone.

Similarly, an electron microscope can generate an image of what is impossible to be seen by human eyes. Using such an image, for example, an engineer can examine a metal to find a crack line which would be difficult, if not impossible, to find without the imaging device.

The data representations of an object can take a number of different forms. For example, surface data for an object can be captured by an observer's eyes, or by a suitable device such as photometric analysis, a digitizer based on probe sensors, or laser surface scanners. Other imaging data for the object can be two-dimensional x-rays, ultrasound images or volume data sets from computer tomography or magnetic resonance imaging.

Image data representations of objects are perhaps most commonly presented in two dimensions, such as, for example, an x-ray film. It is, however, often necessary to identify anatomical structures in medical imaging data sets in three dimensions and to compare preoperative imaging data with postoperative imaging data. There are a variety of the different methods available to render anatomical structures in three dimensions in general and to define the localization and size of the area of interest, such as a tumor. For example, physicians have used a stereotactic frame to locate a tumor in brain.

Regardless of the specific types of data representations used, it is necessary to match or correlate the data representation of an object with the physical object itself. Otherwise, it would be impossible for medical, engineering or other personnel to make the necessary decisions and perform desired operations accurately.

For instance, it may be desirable to combine the optical display of an object with other data representations, like two-dimensional x-rays, ultrasonic images, volume data sets of computer tomography, magnetic resonance imaging or the like. This form of combined data display can then help a physician to visualize the anatomical structure relative to the patient's body as a physician can see with his bare eyes, and may, in many cases, reduce the need for repeated hazardous x-ray exposures.

By combining imaging data from two different sources, the diagnostic information available to a physician in the combination is more than the sum of its parts. Thus, using a combination of image data, for instance, a physician will be able to locate a blood clot or a tumor exactly, and need not rely upon imagination and/or prediction.

In order to match two volume image data sets like CT or MR, it has been proposed to identify a certain number of anatomically characteristic points and to determine the correlations of said points in both imaging data sets.

By setting up a correlation between the coordinate systems of two image data sets, both volume images can be displayed from the same perspective and on the same scale despite a rotation and/or displacement of one of the two images. This process is called matching.

Several attempts have been made in the past to make matching more convenient and more accurate. One of the known techniques to a person skilled in the art is to use markers on both images which eventually make it possible to match entire images.

In order to simplify the matching, it has been proposed to attach certain markers on the object to be examined, the markers being visible and easily identifiable in both images. These may be probes of suitable material whose positions on x-rays, for example, can easily be determined. In the case of optical displays these probes may also consist of colored markers on the surface of the skin. However, this matching technique only allows for the subsequent representation of two single images.

When it is necessary or desirable to use volume data such as computer tomography or magnetic resonance imaging, matching parameters need to be calculated. In order to calculate the matching parameters all projection and distortion parameters of the volume data sets have to be well defined. As a result, the accurate matching of images is more involved and difficult.

Those skilled in the art have made numerous attempts to correlate different images of an object. Some of the principal efforts are summarized below.

One such apparatus is intended for use to detect abnormalities of the spinal column. At least one defined laser light beam is applied to the left and right back of a subject in parallel with an imaginary spinal line. The projected laser beam is captured by a video camera for future comparison. Whereas the light beams would appear as straight line on a flat surface, the light beams projected on the back characterize the deviation of the spinal column. Because the spatial correlation between camera and light source is known, the deviation of the lines are used to compare and calculate the left and right deviation. However, descriptions of this device do not disclose how volume medical imaging data can be combined with this procedure. The invention appears limited to be used on diagnostic of deviation of the spinal column. It cannot be extended to exactly locate a tumor inside of a body, for example. Also it is not disclosed how the system operates when the patient is in an arbitrary position relative to the apparatus. Furthermore, the video camera is fixed to the apparatus, and does not disclose how the video camera can be freely moved relative to the object. Also it does not use a secondary image source as x-ray, computer tomography or another video camera.

Another reference discloses a system to combine the x-ray representations of the spine with the data of a secondary imaging device for the purpose of diagnostics of vertebral distortion due to the difference in length of legs. In order to reduce the exposure to x-rays, the reference proposes the combination of two imaging data sets by using primary reference members that are attached to the skin. The reference members are placed in a specific location to have a specific relation to given vertebral bodies underneath. The position of these reference members can be detected on the x-rays, but also on the data of the secondary imaging device such as a video camera that visualizes the reference members in the form of color marks. The assumption is that the reference members give an indication about the position of the vertebral body underneath without the necessity to take an x-ray. However, the device for displaying the combined image lacks any control of the three dimensional positioning of the object relative to the imaging devices. It also does not disclose how this invention can be used with volume data such as computer tomography or magnetic resonance imaging. The invention does not disclose how the body or the secondary imaging device can freely move without disturbing the accuracy of the image.

Another reference discloses a device to record the position and movement of bodies by an optoelectric system. The device attaches three (3) reference markers of known spatial distribution to the upper and lower jaw. These targets represent a rigid body and therefore the movement of structures associated with it can be analyzed, like the mandible point. A stylus is used to digitize reference points on the head. However, it is not disclosed how this information could be combined with medical imaging data of arbitrary projection planes. Also it does not use any secondary imaging devices.

A further reference describes an apparatus to establish the spatial relationship among the imaging system, the patient, and the focal plane of a microscope. It discloses a method to project an image into the optics of the operating microscope through a prism. The position of the focal plane of the microscope relative to these structures is tracked by ultrasound sensors. However, the invention does not disclose how to extract and match reconstructed data of two or more images as it is described in this reference. The device, as described, matches the images by overlapping three markers in the image under the microscope to the corresponding markers on the object. The device does not use a pointing device such as an electromagnetic stylus and a computer to reconstruct the image space and match images. The reference does not disclose how the method can be used to align virtual images in real-time. The invention uses only three markers on the object and which are not enough reference points to reconstruct virtual images of the object. Also, the invention does not disclose how a video image or any planar projection image like digital substraction angiography (DSA) with unknown imaging parameters might be reconstructed in three dimension or integrated with the computer tomography imaging data.

In summary, all of the known prior art references fail to disclose how to extract and represent image data set in a virtual image which is overlapping the object in a real time display. Movement of the object often requires a repeated, and generally time-consuming, correlation of the images. Thus, the references do not disclose how to superimpose images when the object is in motion. As a result, prior art devices and methods remain somewhat limited in use and application.

BRIEF SUMMARY AND OBJECTS OF THE INVENTION

In view of the foregoing, it is a primary object of the present invention to avoid the foregoing disadvantages and to provide a system and method which allows the combination and the representation of optical displays in a simple, clear and distinct manner.

Another object of the present invention is to provide a method to display a structural image on a display that is positioned between the object and the observer. A structural image is data reconstructed in 3 dimensions from two or more planar imaging data sets, extracted from volume data like CT or MR, extracted from ultrasound, etc. The structural image is matched to and superimposed on the view of the object in the real time in such a manner that the combined image is updated corresponding to movement of the object and the observer. Each point of the data structure on the display is projected on a position of the display that intersects with the line of sight of the observer's eye to the correlating position of this structure on the object.

Yet another object of the present invention is to provide a method continuously tracking the position of the observer's head and the position of the object relative to a display system. This means that the object or the observer's head can move freely in the recording area. The display unit can be also mobile when another position sensor is attached to the display.

Additionally, it is an object of the present invention to provide a method matching a structural image with the object by using markers on the object that are distinguishable in both a structural image and a visual image.

Consistent with the foregoing objects, and in accordance with the invention as embodied and broadly described herein, a system and method are disclosed in one preferred embodiment of the present invention as providing a transparent display positioned between the object and the observer on which displays a superimposed data image transformed from the structural data by calculating the parameters of a three dimensional matrix with information collected from position sensors. The mathematical parameters of the three dimensional matrix are defined in order to transform the structural image data into the perspective display data. Once the parameters of the three dimensional matrix are established, any points of the structural image can be shown on the display as a virtual image corresponding to the points on the object in real time.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENTS

Figure 1:
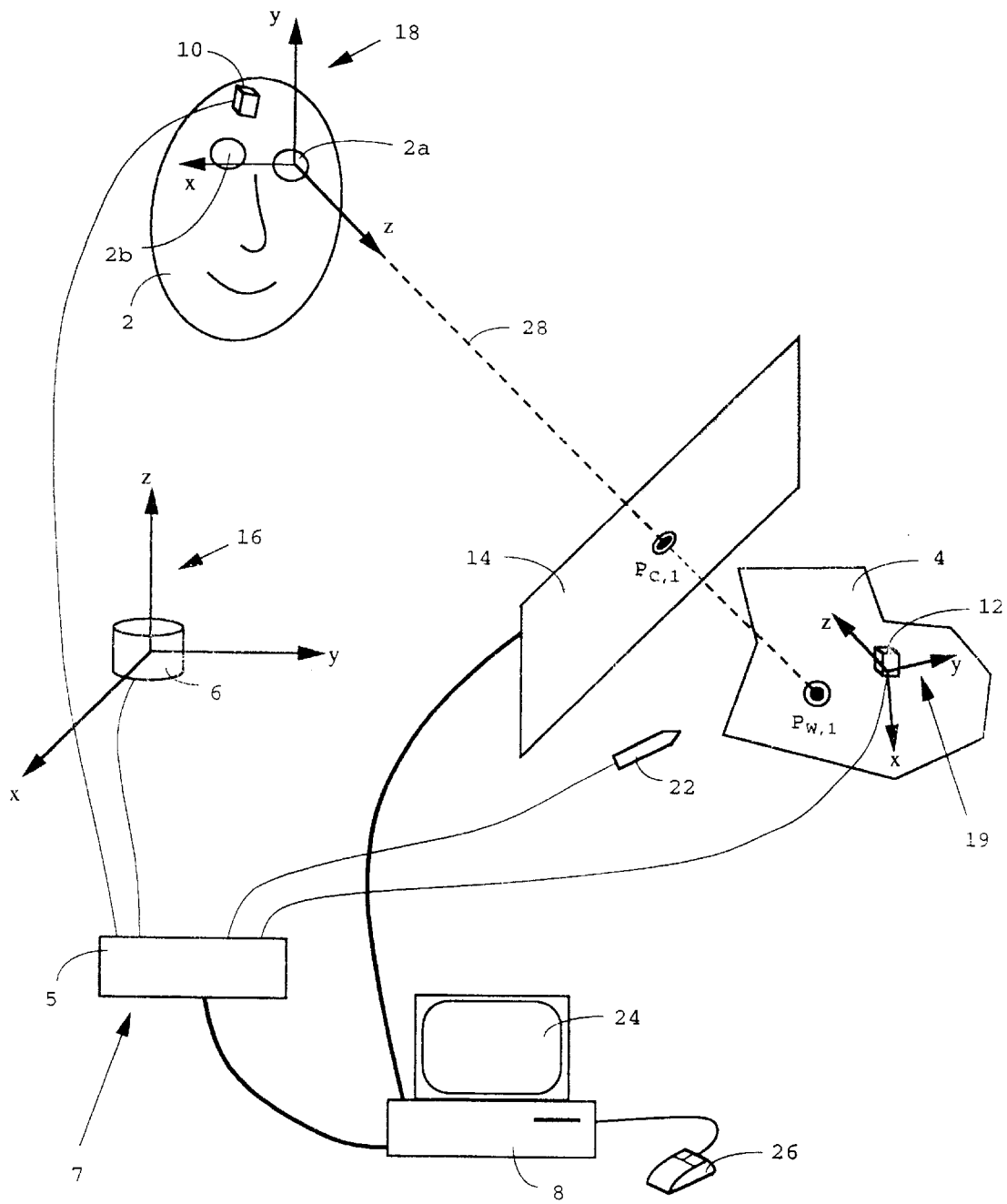
FIG. 1 is a schematic diagram illustrating one presently preferred configuration of the system and method of the of the present invention.
Figure 2:
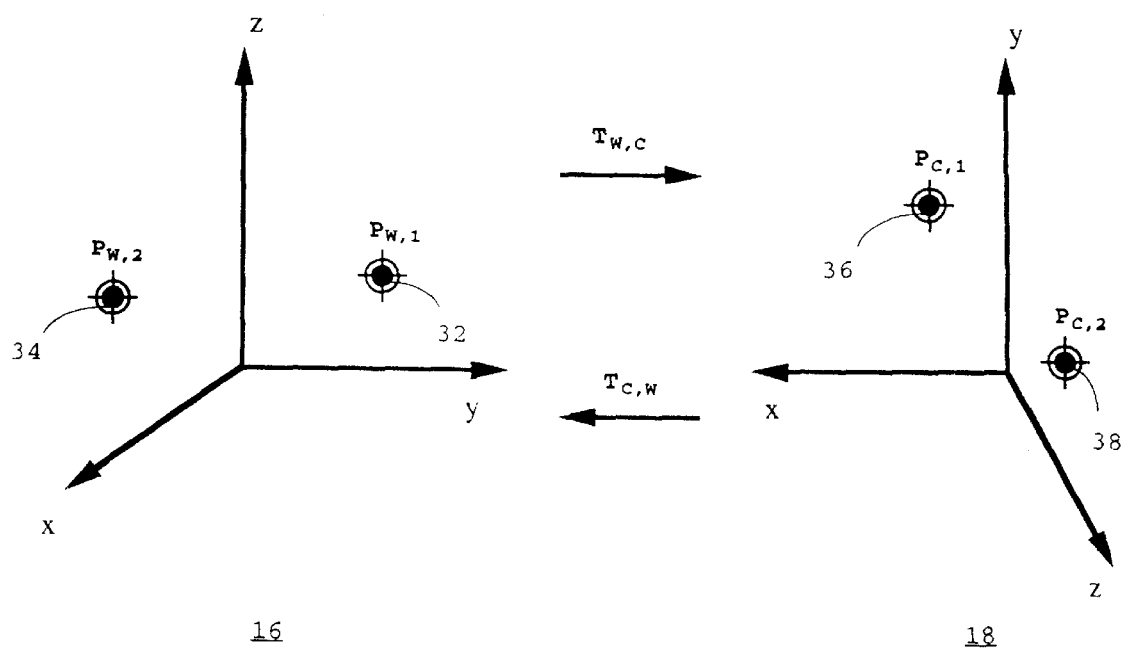
FIG. 2 is a schematic diagram illustrating connector points of an object between the digitizer coordinate system and the observer's coordinate system as employed in accordance with the method of the present invention.

It will be readily understood that the components of the present invention, as generally described and illustrated in the Figures herein, could be arranged and designed in a wide variety of different configurations. Thus, the following more detailed description of the embodiments of the system and method of the present invention, as represented in FIGS. 1 and 2, is not intended to limit the scope of the invention, as claimed, but it is merely representative of the presently preferred embodiments of the invention.

The presently preferred embodiments of the invention will be best understood by reference to the drawings, wherein like parts are designated by like numerals throughout.

This invention has many useful applications in the medical field and in a variety of engineering fields. For example, since the system can locate an area of interest with minimal error, it can be very useful in performing many types of medical surgeries such as stereotactic neurosurgery, spinal surgery or joint replacement surgery.

By way of illustration, the system and method of the present invention can totally eliminate the need for using the conventional bulky stereotactic guide. Instead, only a small size of position sensor such as a electromagnetic sensor needs to be attached to the patient's head. In contrast to conventional techniques, the physician does not need to calculate or measure the distance of a tumor from the skin, and use his/her imaginary coordinate system to locate the tumor inside the patient. Rather, by using the present invention, a physician not only can locate a tumor, but also can see the tumor in virtual image superimposed on his or her view of the patient's head.

Another application of the invention is to be used like a fluoroscopy imaging device without substantial exposure of x-rays. A transparent display located between the patient and a physician can display preoperative x-ray images or data reconstructed from x-rays, and the display can be updated according to the location of the transparent display relative to the patient in order to show x-ray images of interested area.

Referring now to FIG. 1, the observer 2 looks at the object 4 with the eyes 2a and 2b. Attached to the head of observer 2 is a position sensor 10, preferably a magnetic sensor. Another position sensor 12 is attached to the object 4. The sensors 10 and 12 detect a signal from electromagnetic field source 6, e.g. low frequency electromagnetic signal source. The sensors 10 and 12 transmit measurements of positions of the observer's head 2 and the object 4 respectively to a computer 8, which calculates the relative position of object 4 and observer 2.

The computer 8 continuously calculates the perspective projection of the data structure, e.g. the data from an x-ray of object 4, according to the information received from the sensors 10 and 12, and transmits the result to the transparent display 14. As a result, viewing the object 4 through the display 14, observer 2 can see the x-ray or other data image superimposed upon and correlated to the observer's optical surface view of object 4.

Three different coordinate systems are preferably defined as shown in FIG. 1. The digitizer coordinate system 16 can be preferably defined at the origin of the electromagnetic field such as the source 6. Another coordinate system can be defined at the one of the observer's eyes referred as observer's coordinate system 18. The local coordinate system 19 is preferably defined at the position sensor 12.

The computer 8 correlates points in the digitizer coordinate system 16 to data points in the observer's coordinate system 18. Computer 8 also correlates points in the digitizer coordinate system 16 and the structural image data after a calibration process is performed, as described further below.

The calibration is a process to teach the computer 8 how the object 4 in the digitizer coordinate system 16 is perceived by the observer 2. A marker point on the object 4 is digitized with a electromagnetic pointing device such as a stylus 22. The markers are shown in an arbitrary location on the display 24 of computer 8 as a graphic cross hair symbol. Then the observer matches the markers to the corresponding points of the object 4 as the observer can see through the display.

The transparent display 14 is placed between the head of the observer 2 and the object 4. The observer can see the object 4 through the transparent display 14 on which shows the structural image superimposed on the object. The structural image of the object 4 can be an image taken by an imaging device such as x-rays, ultrasound, computer tomography and magnetic resonance imaging. Therefore, the structural image can be referring to two dimensional x-ray images, ultrasound images, computer tomographic images or magnetic resonance images.

Any movement of the observer's head or the object 4 relative to the transparent display 14 is detected and the structural image displayed on display 14 is updated by computer 8 accordingly. Therefore, the observer 2 or the object 4 can be moved freely, and the observer can see the structural images exactly superimposed onto the object 4. Optionally, the display 14 can also be moveable when a sensor transmits the spatial position and orientation of this display 14 to the computer 8.

By way of further detailed explanation and illustration, it is often required to compare preoperative imaging data with intraoperative imaging data in certain surgical procedures. The preoperative image could be an x-ray image, ultrasonic image, tomographic image or magnetic resonance image. At least six markers preferably applied to the surface of the skin such as color markers or radiopaque markers, which are detectable with the preoperative imaging device. The size of the markers on the object 4 are preferably as small as can be reasonably detectable both by the imaging device and by the human eye. The location of the markers are preferably on thin soft tissue area so that the movement of soft tissue due to shift of markers caused by the extension or reflection of the part of body.

It is also possible that anatomical characteristic points may be used as marker points without attaching extra material, such as one end of clavicle, edge of eye or tip of cervical vertebrae.

Then the structural image data is collected by a imaging device, such as for example, x-ray, computer tomography, magnetic resonance, or ultrasound. The markers are preferably located to a surface which the observer eventually can see from the same direction as the intraoperative image. When the structural images are taken by a imaging device, the markers preferably can be identifiable in the image by the human eye.

Some imaging devices interfaced with a computer are capable of transferring data through a video interface output from the controlling computer. Some of the imaging devices have capability of transferring the image data thorough a data storing media such as a magnetic tape, a floppy disk or optical disk. Therefore, the image data can be transferred to the computer 8 used in this invention by means of direct connection or media such as diskette, tape, or optical disk.

In the case that the image data are transferred through direct connection between the imaging device and the computer, a video interface board in the computer converts the analog video signals to digital signals to be stored and used in the computer 8.

In the case that the image data are transferred through a media such as a diskette, a tape or optical disk, the image data stored in the magnetic media or optical media are read by a proper driver attached to the computer such as a disk driver, a tape driver or optical disk driver.

As it is mentioned above, three coordinate systems are preferably defined in the invention. The digitizer coordinate system 16 is defined as the origin of the coordinate system starts from the root of the electromagnetic field such as the source 6. The x and y axis of coordinate system 16 preferably can be defined parallel to the earth surface, and the associated z axis preferably can be defined vertical to the earth surface.

A second coordinate system 18 can be originated from one of the observer's eyes. The z axis of coordinate system 18 preferably can be defined as same direction as the line of view of the object from the observer's eye, and the associated x and y axes can be defined to be orthogonal to z axis as it is shown in FIG. 1. By locating the z axis of coordinate system 18 so as to be lined up with the line of view 28, a matrix conversion process of three dimensions can be simplified. The matrix conversion will be explained in details later in this section.

A third coordinate system 19 can be defined on the object 4. The preferred embodiment of this invention is that the object coordinate system 19 is defined to start its origin from the position sensor 12 such as an electromagnetic sensor.

The location and direction of the observer's head and the object 4 should be defined in space in order to show the structural image data properly on the display 14 which is located between the observer's head 2 and the object 4. This can be achieved by a proper calibration process.

The calibration process is divided into two steps. First, the correlation between the digitizer coordinate system 16 and the observer's coordinate system 18 can be defined. In other words, the observer can teach the computer how the points on the object 4 are located on the display 14 as the observer can see the object 4. Next, the correlation between the digitizer coordinate system 16 and the object local coordinates system 19 can be set up by teaching the computer 8 how to match the structural image is displayed on the transparent display to the object 4.

The first step can be achieved with a digitizer system 7 preferably three dimensional electromagnetic digitizer system and the display 14 located between the observer and the object 4. The observer points out a marker on the object 4 with a pointing device such as stylus 22 of the digitizer system 7. When the observer accurately locates a marker with the stylus 22, he/she notifies the computer that a marker point is accurately recognized, for example by hitting a key or clicking a mouse button of the computer. Then, a corresponding point shows up on the transparent display in an arbitrary location. The point shown on the transparent display 14 should be aligned on the line of view 28 of the observer's eye as shown in FIG. 1 in order to teach the computer how the object 4 is shown to the observer. This can be accomplished by dragging the displayed point on the transparent display to the corresponding point on the object 4 as the observer can see it by means of a computer pointing device 26 such as a mouse. This process can be referred as "matching."

In order to accommodate both translational and rotational freedom of movement of the three dimensional object 4, more than six marker points are preferable. Generally, more marker points can establish the better correlation. In accordance with the presently preferred embodiment of the invention, eight marker points are used to establish an optimal correlation between the observer's head 2 and the object 4. More than 15 marker points has been found not to improve the correlation. Accordingly, the process of matching should be repeated for all the marker points which are preferably more than six. Therefore, the correlation between the observer's coordinate system 18 and the digitizer coordinate system 16 is established, and the computer 8 is taught accordingly.

During the first step of the calibration, it is necessary to fix the location of the observer's head 2, the transparent display 14 and the object 4 in order to give accurate information to the computer 8 which is essential to display a structural image exactly superimposed to the object 4. Once the first stage of the calibration is performed, the observer can move the head freely.

The second stage of calibration is to establish correlation between the structural image and the object 4 in order to show the structural image on the transparent display exactly superimposed to the object. The purpose of the second stage of calibration is to teach the computer the position of reference points of the object 4 relative to the position sensor 12. In other words, the correlation between the object coordinate system 19 and the digitizer coordinate system 16 can be established. As a result, a point on the object 4 can be displayed as a point on the transparent display 14.

The structural image preferably also contains the image of the reference markers mentioned above. However, since the origin of the object coordinate system 19 is same as the location of the position sensor 12, the number of reference points used for the second stage of calibration may not need be as many as the first stage to establish proper image correlation.

The second stage of calibration can be achieved by matching the reference points shown in the structural image (e.g. the x-ray image) to the points on the object 4. The matching of two corresponding points can be accomplished on a separate computer screen 24 or on the transparent display 14. The structural image with reference points is displayed on the screen or on the transparent display. At this stage of process, the structural image is not superimposed to the object 4 yet. Therefore, the structural image can be displayed anywhere on the transparent display in any size. The purpose of displaying the structural image is to perform matching of the reference points on the structural image with the points on the real object 4.

Since the sensor 12 is attached to the object 4, the position of a point on the object relative to the origin of the object coordinate system 19 is not changed when the position and orientation of the entire object 4 is changed in the digitizer coordinate system 16. The data regarding the position and the orientation of the position sensor 12 is updated continuously, and is known to the computer 8 through the digitizer electronic unit 5. Since the positions of the point and the position sensor 12 are fixed to the object 4, the relative position of a point from the position sensor is always the same no matter where the object is located. By defining the object coordinate system 19 starting from the same position as the position sensor 12, the position of a point relative to the object coordinate system 19 is always the same. Therefore, any points on the object can be defined relatively to the object coordinate system 19. Thus, if the location of the position sensor 12 can be identified in the structural image, the position of any points in the structural image relative to the position sensor in the same structural image is always the same.

The preferred embodiment of the invention to find the location of the position sensor 12 in the structural image is to use a back projection technique by which the location can be found retroactively by several markers just like locating a source of a sound by drawing lines from different directions. In order to locate a position by the back projection technique, three reference points relative to the origin of the source may be necessary. However, the preferred embodiment of the invention is to use four (4) reference points for more accurate location of the position sensor in the structural image. Even though the position sensor 12 is imaged in the structural image, the accurate location of the position sensor 12 in the structural image is difficult to identify because it is typically relatively large compared to reference points in the structural image.

Once the location of the position sensor 12 is identified in the structural image, any points in the structural image can be defined relatively to the location of the position. If the correlation between the points in the structural images in the digitizer coordinate system 16 and the points on the object 4 in the object coordinate system 19 is established, the structural image can be moved accordingly as the object moves. For example, when the object 4 moves parallel to the transparent display 14, the location of the position sensor in the structural image moves to the same direction and the all points in the structural image moves along with the equivalent image of the position sensor.

However, identifying the accurate position of the sensor 12 is critical to correlate the structural image and the object 4. Therefore, the accurate sensor position needs to be established first in the structural image. This can be achieved by matching three or more reference points on the object 4 between the structural image and the real object 4. By identifying three reference points in the object 4 and identifying corresponding points in the structural image, the position of the sensor in the structural image relative to each reference point can be identified from the known positions of the reference points relative to the sensor 12 in the object 4. Consequently, after the position of the sensor 12 is identified in the structural image by back projection method, a point can be defined relative to the position sensor in the structural image in the digitizer coordinate system 16.

The matching of the second calibration step can be initially accomplished by moving the stylus to a reference point on the object 4. The matching process is similar to the matching process of the first stage of calibration. When the reference point is accurately pointed with a pointing device such as the stylus 22, the observer notifies the computer 8 that the reference point is recognized, for example, by hitting a key or clicking a mouse button. A corresponding point appears on the structural image which is displayed on the computer screen 24 or the transparent display 14. Then, the observer drags the displayed point to a corresponding reference point on the structural image. The process needs to be repeated until all needed reference points are matched (which are, as mentioned above, preferably four points).

As mentioned above, at least three reference points are necessary to establish the origin of the local coordinate system 19 in the structural image, but four reference points are preferable to establish a accurate position for the method. These reference points can be the same points as is used in the first stage of calibration, or it can be totally different points from the first stage calibration. However, these points should be recognizable both in the structural image and in the object 4.

Through the above-outlined two step the calibration process, the correlation between the observer's view and the object 4, and the correlation between the structural image of the object and the real object are established.

Once the system is calibrated, when the observer moves, the structural image on the transparent display 14 can move accordingly. Even though the observer is looking at the object 4 at an angle, the structural image is displayed as it matches the view of the object by the observer. The structural image is also updated as the object 4 moves. If the structural image contains volume data such as computer tomograph or magnetic resonance image, the structural image on the transparent display can be displayed as it matches the direction and the orientation of the object 4. Therefore, through this invention, two or three dimensional structural image data can be shown on the two dimensional transparent display 14 perspectively like the image is captured by a video camera from the observer's eyes.

If a position sensor (not shown) is also attached to the transparent display 14, the position and orientation of the transparent display can be determined in the digitizer coordinate system 16. The position and orientation data are used to calculate the positions of display points on the transparent display in order to superimpose the structural image accordingly. Consequently, the transparent display 14 can also be moved freely as to the object 4 or the observer's head 2, and the structural image is updated according to the position and the orientation of the transparent display. Therefore, a physician can see a patient's x-ray image in real time as he/she moves the transparent display around the patient's body like it can be seen in a fluoroscopy image without exposure to hazardous x-rays.

As mentioned above, in the present preferred embodiment of the invention, a three dimensional digitizer system 7 is used, and particularly uses electromagnetic fields to determine the position and orientation of sensors which are attached to the observer's head 2 and the object 4. The position sensors 10 and 12 are preferably electromagnetic sensors which simultaneously pick up transitional and rotational data which give the six degree of freedom of the object 4 and the observer's head 2. The six degree of freedom are known as transitional movements in x,y,z directions and rotational movements which are azimuth, elevation, and roll which are referred as Euler angles.

The sensed signals become the input to the computer 8, through the digitizer electronics unit 5, in which computes the location of display points of a structural image on the transparent display based on the sensor's position and orientation relative to the electromagnetic source after the system calibration. As a result, the three dimensional digitizer provides the capability to quickly capture the geometry of a three-dimensional non-metallic object and transmit this data to the computer 8. The preferred embodiment of the invention is to use the digitizer system 7 which includes a digitizer electronics unit 5, an electromagnetic field source 6, a stylus 22 and sensors 10 and 12.

The digitizer electronic unit 5 contains the necessary hardware and software for the digitizer system 7 to compute the position and orientation of sensors 10 and 12 and stylus 22. Also it contains analog circuitry to generate and sense the low frequency electromagnetic fields, and digitize the sensed analog signals. Further, it contains a circuitry to generate the digital output in ASCII or binary form to interface with a host computer.

Both the electromagnetic field source 6, and sensors 10 and 12 contain three mutually orthogonal loops (coils). The stylus 22 is another form of a sensor. It is a pen style pointer containing three mutually orthogonal loops like a sensor. The loop diameters are kept very small compared to the distance separating the electromagnetic field source 6 and a sensor so that each loop may be regarded as a point or infinitesimal dipole with respect to the source.

Exciting the electromagnetic field source results in an output at the sensor of a set of three linearly independent vectors. The three output vectors of a sensor contain sufficient information to determine the position and orientation of the sensor relative to the electromagnetic field source 6.

The output of the digitizer electronics unit 5 becomes the input to the computer 8 with a standard interface method such as RS232C serial connection or IEEE-488 interface. The computer has standard peripherals such as a computer screen 24, data storage device, e.g., a hard disk or a floppy disk drive, a keyboard and a pointing device 26, e.g., a mouse or a trackball. The computer preferably has a data storage unit such as a hard disk which is large enough to store data from an imaging device such as computerized tomograph x-ray or magnetic resonance image, and preferably the retrieval time of the storage device is as short as possible for fast access to the image data. Also, a math-coprocessor is preferable since the computer has to perform many mathematical calculations, including matrix conversions. The computer also preferably has a capability of producing another external video signal for the transparent display. In the preferred embodiment of this invention, a Quadra computer manufactured by MacIntosh equipped with an one giga byte hard disk and a CD-ROM drive is used. However, any computer which is fast enough to calculate the necessary mathematics, to display the image on the display and to store abundant data can be used for the invention.

The converted structural image(commonly called a mode), according to the position of the observer and the object 4, is displayed on the transparent display 14. The preferred embodiment of this invention is the use of moveable, transparent LCD display as the display 14. The LCD display is the same display used in many laptop computers. The LCD display is preferably located close to the object 4, similarly an x-ray screen used in radiology, to minimize the difference of the view by right and left eyes.

Also, the transparent display 14 can be a head up display which is attached to a physician's head. The graphic data can be projected onto a head up display. Since the head of the physician has a reference sensor attached, the position of the eyes relative to the digitizer coordinate system 16 is defined. As like the LCD transparent screen, when a physician moves his head to have a better view of the interested area, a virtual image of the object can be presented on the head up display which is superimposed to the object. The physician can see the structural images of the object 4 as he/she moves his/her head.

From FIG. 2, a point in the observer's coordinate system 18 can be defined as equation 1 using the digitizer coordinate system 16 and the transformation matrix $T_{W,C}$.

$$[X_{C,i}\ Y_{C,i}\ Z_{C,i}\ P_{C,i}] = [X_{W,i}\ Y_{W,i}\ Z_{W,i}\ 1] \times T_{W,C} \quad \text{(Eq.1)}$$

Where, $$T_{W,C} = \begin{bmatrix} T_{1,1} & T_{1,2} & T_{1,3} & T_{1,4} \\ T_{2,1} & T_{2,2} & T_{2,3} & T_{2,4} \\ T_{3,1} & T_{3,2} & T_{3,3} & T_{3,4} \\ T_{4,1} & T_{4,2} & T_{4,3} & T_{4,4} \end{bmatrix} \quad \text{(Eq. 2)}$$

If $T_{1,1} = T_{2,2} = T_{3,3} = 1$ then no scaling difference occurs between the digitizer space and the observer's space. $T_{1,4}$, $T_{2,4}$, $T_{3,4}$ give the perspective distortions, for a observer's sensor located on the X, Y, and Z axis respectively. $T_{4,4}$ can be used in a homogeneous matrix solution as an arbitrary scale factor and be defined as unity. In the most general case there are 15 unknowns (the elements of the transformation matrix), so the number of points used to determine $T_{W,C}$ should be a minimum of six (6).

The real picture coordinates of a point in the observer's coordinate system can be expressed as follows:

$$[X^*_{C,i}\ Y^*_{C,i}\ Z^*_{C,i}\ 1] = [X_{C,i}/P_{C,i}\ Y_{C,i}/P_{C,i}\ Z_{C,i}/P_{C,i}\ 1] \quad \text{(Eq.3)}$$

In the real picture coordinate system, only two dimensional components, e.g. x and y, exist. The z component of the digitizer coordinate system is into the term of the x and y components in the real picture coordinate system. From equation 2 and 3, the following can be extracted:

$$X^*_{C,i} \frac{(X_{W,i}T_{1,4} + Y_{W,i}T_{2,4} + Z_{W,i}T_{3,4} + 1)}{X_{W,i}T_{1,1} + Y_{W,i}T_{2,1} + Z_{W,i}T_{3,1} + T_{4,1}} = 1 \quad \text{(Eq. 4)}$$

$$Y^*_{C,i} \frac{(X_{W,i}T_{1,4} + Y_{W,i}T_{2,4} + Z_{W,i}T_{3,4} + 1)}{X_{W,i}T_{1,2} + Y_{W,i}T_{2,2} + Z_{W,i}T_{3,2} + T_{4,2}} = 1$$

Which gives $$X^*_{C,i} = X_{W,i}T_{1,1} + Y_{W,i}T_{2,1} + Z_{W,i}T_{3,1} + T_{4,1} - \quad \text{(Eq. 5a)}$$
$$X^*_{C,i}X_{W,i}T_{1,4} - X^*_{C,i}Y_{W,i}T_{2,4} - X^*_{C,i}Z_{W,i}T_{3,4}$$

$$Y^*_{C,i} = X_{W,i}T_{1,2} + Y_{W,i}T_{2,2} + Z_{W,i}T_{3,2} + T_{4,2} - \quad \text{(Eq. 5b)}$$
$$Y^*_{C,i}X_{W,i}T_{1,4} - X^*_{C,i}Y_{W,i}T_{2,4}\ Y^*_{C,i}Z_{W,i}T_{3,4}$$

From the conversion matrix $T_{W,C}$, assuming that the resulted transformation is normalized, $T_{4,4}$ becomes 1. Also, if the z axis is aligned with the line of view 28 from the observer as it is shown in FIG. 1, and the observer only sees the object as a two dimensional image, $Z_{C,i}$ component from Eq.2 disappears. Therefore, the components of the transformation matrix for the z axis ($T_{1,3}$, $T_{2,3}$, $T_{3,3}$ and $T_{4,3}$) can be substituted with 0s. Consequently, the conversion matrix is left with 11 unknown components which can be calculated by 11 equations or six points both given in the digitizer coordinates and the observer's coordinates. These points are referred as marker points above.

If Eq.4 is applied to six points, a matrix form can be defined as follows:

$$A \times x = b \quad \text{(Eq.6)}$$

where $$A = \begin{bmatrix} X_{W.1} & 0 & -X^*_{C.1}X_{W.1} & Y_{W.1} & 0 & -X^*_{C.1}Y_{W.1} & Z_{W.1} & 0 & -X^*_{C.1}Z_{W.1} & 1 & 0 \\ 0 & X_{W.1} & -Y^*_{C.1}X_{W.1} & 0 & Y_{W.1} & -Y^*_{C.1}Y_{W.1} & 0 & Z_{W.1} & -Y^*_{C.1}Z_{W.1} & 0 & 1 \\ X_{W.2} & 0 & -X^*_{C.2}X_{W.2} & Y_{W.2} & 0 & -X^*_{C.2}Y_{W.2} & Z_{W.2} & 0 & -X^*_{C.2}Z_{W.2} & 1 & 0 \\ 0 & X_{W.2} & -Y^*_{C.2}X_{W.2} & 0 & Y_{W.2} & -Y^*_{C.2}Y_{W.2} & 0 & Z_{W.2} & -Y^*_{C.2}Z_{W.2} & 0 & 1 \\ X_{W.3} & 0 & -X^*_{C.3}X_{W.3} & Y_{W.3} & 0 & -X^*_{C.3}Y_{W.3} & Z_{W.3} & 0 & -X^*_{C.3}Z_{W.3} & 1 & 0 \\ 0 & X_{W.3} & -Y^*_{C.3}X_{W.3} & 0 & Y_{W.3} & -Y^*_{C.3}Y_{W.3} & 0 & Z_{W.3} & -Y^*_{C.3}Z_{W.3} & 0 & 1 \\ X_{W.4} & 0 & -X^*_{C.4}X_{W.4} & Y_{W.4} & 0 & -X^*_{C.4}Y_{W.4} & Z_{W.4} & 0 & -X^*_{C.4}Z_{W.4} & 1 & 0 \\ 0 & X_{W.4} & -Y^*_{C.4}X_{W.4} & 0 & Y_{W.4} & -Y^*_{C.4}Y_{W.4} & 0 & Z_{W.4} & -Y^*_{C.4}Z_{W.4} & 0 & 1 \\ X_{W.5} & 0 & -X^*_{C.5}X_{W.5} & Y_{W.5} & 0 & -X^*_{C.5}Y_{w.5} & Z_{W.5} & 0 & -X^*_{C.5}Z_{W.5} & 1 & 0 \\ 0 & X_{W.5} & -Y^*_{C.5}X_{W.5} & 0 & Y_{W.5} & -Y^*_{C.5}Y_{W.5} & 0 & Z_{W.5} & -Y^*_{C.5}Z_{W.5} & 0 & 1 \\ X_{W.6} & 0 & -X^*_{C.6}X_{W.6} & Y_{W.6} & 0 & -X^*_{C.6}Y_{W.6} & Z_{W.6} & 0 & -X^*_{C.6}Z_{W.6} & 1 & 0 \end{bmatrix} \text{ and}$$

$$x = \begin{bmatrix} T_{1.1} \\ T_{1.2} \\ T_{1.4} \\ T_{2.1} \\ T_{2.2} \\ T_{2.4} \\ T_{3.1} \\ T_{3.2} \\ T_{3.4} \\ T_{4.1} \\ T_{4.2} \end{bmatrix}$$

$$b = \begin{bmatrix} X^*_{C.1} \\ Y^*_{C.1} \\ X^*_{C.2} \\ Y^*_{C.2} \\ X^*_{C.3} \\ Y^*_{C.3} \\ X^*_{C.4} \\ Y^*_{C.4} \\ X^*_{C.5} \\ Y^*_{C.5} \\ X^*_{C.6} \end{bmatrix}$$

From Eq.6, the transformation vector x can be found by known positions of preferably six points. Once the vector x is determined, any points on the structural image displayed on the transparent display can be transformed to a point on the transparent display 14 in the line of view 28 of the object 4 from the observer's eye 2a.

The present invention has many different applications and may be useful in a number of different disciplines. For example, on many occasions, an instrument needs to be inserted to operate on an area. If a position sensor is attached to the instrument, the instrument is also shown on the transparent display 14 as a part of the virtual image. The position sensor on the instrument transmits the translational and rotational data of the instrument to the computer 8 through the digitizer 7. Therefore, a physician can locate the instrument with respect to the area of interest with great accuracy.

Another possible application is to use a video camera at the location of the physician's eye and a computer screen instead of the transparent display which shows the virtual image of the object. A position sensor is attached to the video camera. This allows for the display of several images from different angle at the same time. For example, frontal and lateral positions of the object can be shown in one screen, and the physician can observe the position changes from different views simultaneously corresponding to the movement of the object and the video camera. This embodiment can be referred as the 4View Plane.

A further application is to use an endoscope instead of a video camera. If a position sensor is attached to the endoscope and a structural image is combined with the endoscope image, the superimposed structural image can be updated as the endoscope goes through a human organ, such as the tracheal tube. Also it is possible to superimpose the edge of an organic tubing on the endoscope image in order to guide the endoscope. This can be referred as the live video fusion. If the live video fusion is combined with the 4View plane concept, a physician is not only able to see a path for the endoscope, but also can see the side view of the path showing how the endoscope is going down.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by united states letters patent is:

1. A method for displaying a moveable body in real time in three spatial dimensions, the method comprising the steps of:

continuously tracking the position of said body, an observer, and a display unit relative to each other;

continuously calculating a three-dimensional perspective projection of an image data representation of said body using data from the position tracking step; and displaying said projection of said image data representation on a display device to correlate the data representation to a perception of the body by the observer, said correlation comprising:

matching the position, perspective, and scale of the data representation to those of a three-dimensional structural image of the body by detecting the body and presenting the structural image to the perception of the observer; and displaying the data representation on a transparent display device positioned between the structural image of the body and the observer.

2. The method of claim 1 further comprising providing a sensor for detecting relative motion between the body and an imaging device presenting an image to the observer for correlating the model to an image of the body perceived by the observer.

3. The method of claim 2 wherein the sensor is selected to detect motion in six degrees of freedom.

* * * * *